United States Patent [19]

Preston et al.

[11] 4,165,432
[45] Aug. 21, 1979

[54] PEROXY DI-ESTER POLYOLS

[75] Inventors: Frank J. Preston, Meriden; Theodore C. Kraus, Cheshire; Kiran B. Chandalia, Hamden, all of Conn.

[73] Assignee: Olin Corporation, New Haven, Conn.

[21] Appl. No.: 843,103

[22] Filed: Oct. 18, 1977

[51] Int. Cl.$^2$ .................. C07C 69/34; C07C 69/42
[52] U.S. Cl. ........................... 536/4; 525/123; 525/172; 525/437; 521/137; 526/200; 526/209; 526/213; 526/216; 526/227; 526/232; 528/271; 528/301; 560/85; 560/86; 560/87; 560/88; 560/89; 560/90; 560/91; 560/193; 560/194; 560/196; 560/197; 560/198; 536/119; 536/120
[58] Field of Search ............. 560/89, 91, 90, 198, 560/86, 85, 87, 88, 193, 194, 196, 197; 536/4

[56] References Cited

U.S. PATENT DOCUMENTS

| | | | |
|---|---|---|---|
| 3,383,351 | 5/1968 | Stramberger | 260/33.2 |
| 3,652,639 | 3/1972 | Pizzini et al. | 260/465 X |
| 3,671,651 | 6/1972 | D'Angelo | 560/89 |
| 3,823,201 | 7/1974 | Pizzini et al. | 260/861 |

*Primary Examiner*—Jane S. Myers
*Attorney, Agent, or Firm*—Robert J. Feltovic; Thomas P. O'Day

[57] ABSTRACT

Compounds containing peroxy linkages connecting similar polyol ester constituents are described. These peroxy di-ester polyols are prepared by the direct esterification of peroxy diacids with polyols, in the presence of a strong mineral acid catalyst. The peroxy di-ester polyol products function as free radical initiators and grafting bases in the graft copolymerization of unsaturated monomers with polyols. These graft copolymers are useful in the formulation of polyurethanes.

3 Claims, No Drawings

PEROXY DI-ESTER POLYOLS

It is well known in the art to employ independent free radical type catalysts to initiate reaction of unsaturated polyols and vinyl monomers to form graft copolymer dispersions. Suitable free radical type vinyl polymerization catalysts include persulfates, perborates, azo compounds, and peroxides. Further discussion of the use of such catalysts to form graft copolymer dispersions and a listing thereof appears in U.S. Pat. No. 3,931,450.

Co-pending application Ser. No. 780,213, filed Mar. 22, 1977, now U.S. Pat. No. 4,094,868, describes novel polyol compounds featuring azo linkages which have been incorporated within the polyol itself. These linkages decompose at elevated temperatures to provide free radical grafting sites in subsequent use of the polyols for graft copolymerization with unsaturated monomers, and thereby eliminate the need for independent free radical catalysts.

Novel peroxy di-ester polyols have now been developed which are particularly useful in the preparation of graft copolymers for polyurethane end uses. These novel peroxy compounds can be represented by the general formula:

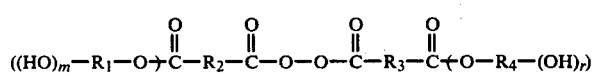

wherein:
m and r independently are integers from 1 to 5;
$R_2$ and $R_3$ independently represent radicals selected from aryl and alkenyl having 2 to 5 carbon atoms; and groups $((HO)_m-R_1-O\text{)}$ and $(O-R_4-(OH)_r)$ independently are residues of polyols, wherein $R_1$ and $R_4$ are independently selected from polyether or polyester chains, after removal of one hydroxy hydrogen therefrom.

These peroxy compounds can be prepared by a single-step esterification method comprising direct esterification of peroxy diacids with polyols, in the presence of a strong mineral acid.

The peroxy di-ester polyols of the present invention include multiple terminal hydroxyl groups which make them particularly useful in preparing graft copolymers for polyurethane end use formulations.

The peroxy di-ester polyols of the above formula include both symmetrical and non-symmetrical peroxy di-ester polyol compounds. Symmetrical peroxy-bis ester polyols can be prepared by reacting a peroxy-bis diacid with a polyol. Unsymmetrical peroxy di-ester polyols also can readily be formulated by reacting an unsymmetrical peroxy diacid with a polyol or a mixture of polyols or by reacting a peroxy-bis diacid with a mixture of polyols. The symmetrical "peroxy di-ester polyols", hereinafter referred to as peroxy-bis ester polyols, are preferred. In order to simplify the presentation herein, the peroxy-bis ester polyols have been selected to be discussed in more specific detail below. The principles presented are readily adaptable to unsymmetrical peroxy di-ester polyols. The peroxy-bis ester polyols of the present invention can be represented by the general formula:

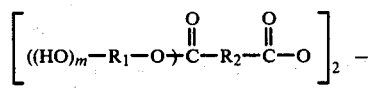

wherein: m, $R_2$, and $((HO)_m-R_1-O\text{)}$ are as defined above.

Particularly preferred are peroxy-bis ester polyols of the formula:

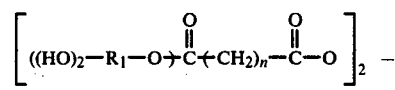

wherein:
n is 2 to 4; and
$((HO)_2-R_1-O\text{)}$ is the residue of a polyether triol after removal of one hydroxy hydrogen therefrom.

The peroxy di-ester polyol compounds can be prepared by directly esterifying a polyol with a suitable peroxy diacid.

Any peroxy diacid may be used. These non-cyclic diacyl peroxides of dibasic acids are properly named as carboxy-substituted diacyl peroxides. Typically preferred peroxy-bis diacids which may be used include succinic acid peroxide, [di(3-carboxy propionyl) peroxide], glutaric acid peroxide, [di(4-carboxy butryl peroxide], adipic acid peroxide, [di(5-carboxypentanoyl) peroxide] pimelic acid peroxide, [di(6-carboxyhexanoyl) peroxide], suberic acid peroxide, [di(7-carboxyheptanoyl) peroxide], phthalic acid peroxide, [di(2-carboxylbenzoyl) peroxide], and the like. The preferred peroxy-bis diacid is glutaric acid peroxide. The peroxy-bis diacid reactant commonly can be prepared by oxidation of suitable acid anhydrides with hydrogen peroxide, according to known procedures.

The polyol reactant which is used in preparing the peroxy di-ester polyols of the invention can be any such compound, including mixtures of two or more such compounds, having 2-6 hydroxyl groups and preferably an average equivalent weight from about 250 to about 5000. This includes polyester polyols and polyether polyols. However, the polyether polyols are generally preferred.

The polyester polyols include the products of reacting polycarboxylic acids with polyhydric alcohols. Illustrative polycarboxylic acids include, for example, oxalic, malonic, succinic, glutaric, adipic, pimelic, suberic, azelaic acid and the like. Illustrative polyhydric alcohols include various diols, triols, tetrols and higher-functionality alcohols, such as ethylene glycol, 1,3-propylene glycol, 1,2-propylene glycol, butylene glycols, butane diols, pentane diols, glycerol, trimethylolpropane, trimethylolhexane, pentaerythritol, sorbitol, hexane 1,2,6-triol, 2-methyl glucoside, mixtures thereof and the like. Aromatic type polyols such as Bisphenyl A may also be used.

The polyether polyols, the use of which is preferred herein, include various polyoxyalkylene polyols and mixtures thereof. These can be prepared, according to well-known methods, by condensing an alkylene oxide, or a mixture of alkylene oxides using random or stepwise addition, with a polyhydric initiator or mixture of initiators. Illustrative alkylene oxides include ethylene oxide, propylene oxide, butylene oxide, amylene oxide, aralkylene oxides such as styrene oxide, and the halogenated alkylene oxides such as trichlorobutylene oxide and so forth. The most preferred alkylene oxide is propylene oxide or a mixture thereof with ethylene oxide using random or step-wise oxyalkylation.

The polyhydric initiators used in preparing the polyether polyol reactant can be any such material which has from 2 to 6 active hydrogens. This includes (a) aliphatic diols such as ethylene glycol, 1,3-propylene glycol, 1,2-propylene glycol, butylene glycols, butane diols, pentane diols, and the like, (b) the aliphatic triols such as glycerol, trimethylolpropane, triethylolpropane, trimethyolhexane, and the like, (c) higher-functionality alcohols such as sorbitol, pentaerythritol, methyl glucoside, and the like, (d) the polyamines such as tetraethylene diamine and (e) the alkanolamines such as diethanolamine, triethanolamine and the like.

A preferred group of polyhydric initiators for use in preparing the polyether polyol reactant is one which comprises aliphatic triols such as glycerol, trimethylolpropane and the like.

The alkylene oxide—polyhydric initiator condensation reaction is preferably carried out in the presence of a catalyst such as KOH as is well known in the art. In effecting the reaction, a sufficient proportion of alkylene oxide is used as to provide a final polyol product having an average equivalent weight of about 250–5000, preferably about 700–3000 and more preferably about 1000–1500. The catalyst is thereafter preferably removed, leaving a polyether polyol which is ready for use in preparing the peroxy di-ester polyols of the invention.

It has been found that, in an appropriate reaction setting, the peroxy diacid, as defined above, can successfully be made to directly esterify with polyols. By conducting the esterification in a solution including about 0.1 to 10 percent by weight, based on total weight of the polyol and peroxy diacid reactants, of a mineral acid, such as sulfuric, phosphoric or hydrohalic acid, the peroxy diacid and polyol can be forced to esterify. In particular, hydrochloric acid has been found to be preferable, since it can readily be removed from the peroxy di-ester polyol product. Common clean-up procedures such as purging the product with an inert gas (e.g., nitrogen) and/or silicate clay treatment and filtering can be utilized to remove this acid catalyst. About one to about five percent acid concentration has been found to result in advantageous yields.

To diesterify the peroxy diacid reactant, two moles of polyol reactant are required per mole of diacid. However, to shift the equilibria of the esterification reaction to more favorable ester yield, use of excess polyol is preferred. A molar ratio of polyol to diacid of from about 2.5 to about 5:1 is particularly preferred. The excess unreacted polyol preferably may be allowed to remain with the product to result in a peroxy di-ester polyol—unreacted polyol mixture, which is then used in the graft copolymerization reaction described hereinafter.

The direct esterification reaction is conducted by heating the peroxy diacid mixed with the polyol in the presence of the mineral acid catalyst. If a gaseous acid catalyst, such as the preferred HCl, is utilized, the catalyst can be conveniently bubbled through the reaction mixture as the reaction progresses. Proper reaction temperatures vary with reactants but normally range between about 40° C. and about 70° C. Care must be exercised to keep the reaction temperature below the temperature at which the selected peroxy diacid decomposes, so that the peroxy linkages are not ruptured. Reaction temperatures of about 40° to 50° C. are particularly preferred.

Initially, the peroxy diacid reactant is insoluble in the polyol reactant. As the reaction progresses, the diacid is esterified with the polyol until the reaction solution gradually becomes clear. To ensure complete reaction, post-reaction conditions are maintained for several hours.

Alternatively, the peroxy di-ester polyols of the subject invention can also be prepared by transesterification of a peroxy diacid ester with a polyol. In this procedure, the peroxy diacid first is diesterified with a low molecular weight alcohol, such as methanol. The diester then is transesterified in the presence of a catalyst, such as sodium methoxide, with the polyol, whereby the polyol radical exchanges places with the methyl group.

Direct esterification features distinct advantages over other methods, since, for example, single-step esterification from the diacid is more economical.

To form graft copolymers, the peroxy di-ester polyols are treated with an ethylenically unsaturated monomer or mixture of such monomers, usually in the presence of additional polyol. The monomers useful in the copolymerization process are polymerizable monomers characterized by the presence of at least one polymerizable ethylenic unsaturated group of the type $>C=C<$. Such monomers are exemplified by those described in U.S. Pat. No. 3,383,351, Column 4, Lines 61–75 and Column 5, Lines 1–40. Preferred monomers include styrene, acrylonitrile, vinyl chloride, methyl methacrylate, hydroxy ethyl acrylate, butadiene, isoprene, chloroprene, and the like. In particular, styrene and acrylonitrile have been found to be preferred. The reaction temperature for copolymerization should be above the thermal decomposition temperature of the particular peroxy di-ester employed. Such temperatures normally will range from about 70° to 150° C. Additional free radical catalyst is not required, as the peroxy linkage within the chain of the peroxy di-ester polyol itself is broken at the reaction temperature and the free radicals formed serve as suitable catalysts for initiating the monomer polymerization. Hence, grafting of the vinyl monomers takes place directly on the polyol chain at the site of the severed bond. This eliminates dependency of grafting through hydrogen abstraction alone. The overall grafting reaction can be characterized by the following, wherein m, $R_1$, and $((HO)_m-R_1-O)$ are as defined in Formula II above:

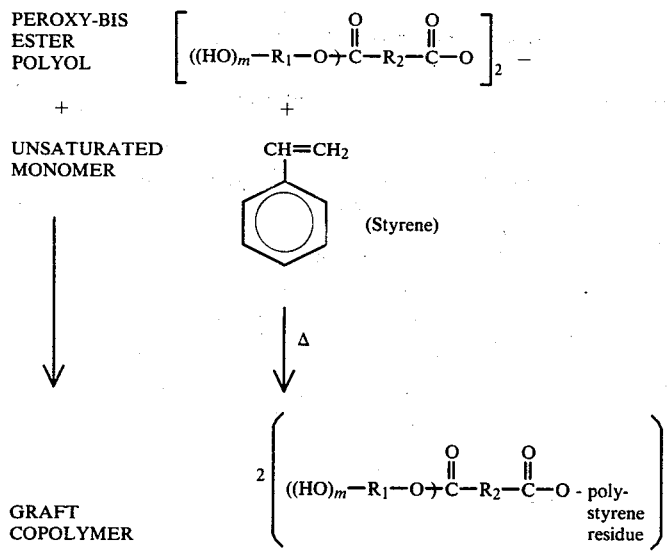

The graft copolymers formed are particularly suited for use in polyurethane formulations. Presence of multiple terminal hydroxyl groups allows for reaction with polyisocyanates. Modification of the amount of terminal hydroxyls results in variation of the degree of branching and cross-linking in the resulting polyurethane products. Accordingly, desired physical properties can be manipulated.

The following examples are provided to further illustrate the invention. All parts and percentages are by weight unless otherwise specified.

Preparation of Polyether Polyol Reactants a. Polyether triol A was prepared from glycerol by base catalyzed block addition of propylene oxide capped with ethylene oxide such that the ethylene oxide content was approximately 9.8% and the primary hydroxyl content was approximately 55%. Final OH number was 37 mg KOH/g.

b. Polyether triol B was prepared from glycerol by base catalyzed random addition of propylene oxide and ethylene oxide such that the ethylene oxide content was approximately 5% and the primary hydroxyl content was approximately 0%. Final OH number was 56.

c. Polyether triol C was prepared from glycerol by base catalyzed block addition of propylene oxide capped with ethylene oxide such that the ethylene oxide content was approximately 11% and the primary hydroxyl content was approximately 55%. Final OH number was 56.

Preparation of Peroxy-Bis Ester Polyols

EXAMPLE I 2.9 g of glutaric acid peroxide was mixed in a 500 ml three-neck flask with 250 g of polyol A. This is a 5:1 molar ratio of polyol to peroxy acid. The flask was fitted with an inlet sparge tube for gaseous HCl, a mechanical stirrer, a thermometer and an outlet tube for HCl, which was vented into a drain with constant water flow. The flask was heated by an oil bath to 40° C. and HCl flow begun. An exotherm was noted and the temperature rose to 50° C. where it was maintained with moderate HCl flow. After 45 minutes, the peroxy acid gradually dissolved and the clear solution was maintained at 50° C. for an additional 30 minutes.

Nitrogen gas was then passed through the sparge tube while maintaining temperature at 40°–45° C. From time to time, the exit stream was tested with wet litmus paper to detect traces of HCl; however, a more sensitive indicator was odor. After three to four hours, HCl elimination was complete. A vacuum was then imposed on the system for 15 minutes to remove all gases from the system. A sample of peroxy-bis ester polyol A was withdrawn for various analyses.

| Gel Permeation Chromatography | OH No. mg KOH/g | Acid No. mg KOH/g |
|---|---|---|
| 74% 5100 (M.W.) 25.9% 7800 (M.W.) | 30.1 | 0.81 |

EXAMPLE II

Polyol A was again reacted using the same general scheme as outlined above, employing however a 2.5:1 molar ratio of polyol to peroxy acid. Analyses of the final product yielded the following data:

| Gel Permeation Chromotography | OH No. mg KOH/g | Acid No. mg KOH/g |
|---|---|---|
| 72.8% 5100 (M.W.) 27.2% 7500 (M.W.) | 23.2 | 4.18 |

EXAMPLE III

Polyol B was reacted using the same general scheme as outlined above. A 2.5:1 molar ratio of polyol to peroxy acid was used. Analyses of the final product yielded the following data:

| Gel Permeation Chromatography | OH No. mg KOH/g | Acid No. mg KOH/g |
|---|---|---|
| 58.3% ~2800 (M.W.) | 27.6 | 5.74 |

| Gel Permeation Chromatography | OH No. mg KOH/g | Acid No. mg KOH/g |
|---|---|---|
| 41.7% ~ 5500 (M.W.) | | |

EXAMPLE IV

Polyol C was reacted using the same general scheme as outlined above. A 2.5:1 molar ratio of polyol to peroxy acid was used. Analyses of the final product yielded the following data:

| Gel Permeation Chromatography | OH No. mg KOH/g | Acid No. mg KOH/g |
|---|---|---|
| 26.3% ~ 2500 (M.W.) | 23.6 | 2.71 |
| 73.7% ~ 7700 (M.W.) | | |

We claim:

1. A peroxy bis-ester polyol characterized by the formula:

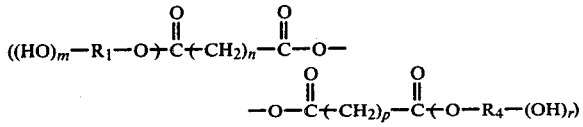

wherein:
m and r are the same and represent the integer 2;
n and p are the same and represent an integer from 2 to 4; and
$((HO)-R_1-O-)$ and $(-O-R_4-(OH)_r)$ are the same and represent residues of polyether polyols, $R_1(OH)_{m+1}$ and $R_4(OH)_{r+1}$, wherein $R_1$ and $R_4$ represent polyether chains having an average equivalent weight of from about 700 to 3000, after removal of one hydroxy hydrogen therefrom.

2. The compound of claim 1 wherein n and p are the same and represent the integer 3.

3. The compound of claim 2 characterized by the formula:

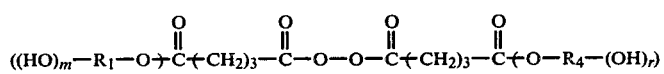

wherein:
m and r are the same and represent the integer 2, and $((HO)_m-R_1-O-)$ and $(-O-R_4-(OH)_r)$ are the same and represent a residue of a polyether triol having an equivalent weight of about 1000 to 1500 after removal of one hydroxy hydrogen therefrom.

* * * * *

UNITED STATES PATENT AND TRADEMARK OFFICE
CERTIFICATE OF CORRECTION

PATENT NO. : 4,165,432
DATED : August 21, 1979
INVENTOR(S) : Frank J. Preston, Theodore C. Kraus and Kiran B. Chandalia It is certified that error appears in the above-identified patent and that said Letters Patent are hereby corrected as shown below:

Column 4, line 44, "$>C = C<$" should read -- $\left.\right>C = C\left.\right<$ --.

Signed and Sealed this

Twelfth Day of February 1980

[SEAL]

Attest:

SIDNEY A. DIAMOND

Attesting Officer

Commissioner of Patents and Trademarks